United States Patent [19]

Lindegaard et al.

[11] Patent Number: 5,389,307
[45] Date of Patent: Feb. 14, 1995

[54] DETERGENT COMPOSITION COMPRISING AN ALKYL SULFATE AND A SUBSTILISIN VARIANT

[75] Inventors: Poul Lindegaard, Copenhagen; Dorrit A. Aaslyng, Roskilde, both of Denmark

[73] Assignee: Novo Nordisk A/S, Bagsvaerd, Denmark

[21] Appl. No.: 39,042

[22] PCT Filed: Nov. 14, 1991

[86] PCT No.: PCT/DK91/00342

§ 371 Date: Apr. 6, 1993

§ 102(e) Date: Apr. 6, 1993

[87] PCT Pub. No.: WO92/08778

PCT Pub. Date: May 29, 1992

[30] Foreign Application Priority Data

Nov. 14, 1990 [DK] Denmark .............................. 2714/90

[51] Int. Cl.⁶ .......................... C11D 1/12; C11D 3/386
[52] U.S. Cl. .................... 252/549; 252/174.12; 252/DIG. 12; 435/219; 435/220; 435/221; 435/222
[58] Field of Search .............. 252/174.12, DIG. 12, 252/549; 435/219, 220, 221, 222

[56] References Cited

U.S. PATENT DOCUMENTS

| | | | |
|---|---|---|---|
| 3,790,482 | 2/1974 | Jones | 252/525 |
| 4,760,025 | 7/1988 | Estell et al. | 435/222 |
| 4,914,031 | 4/1990 | Zukowski | 435/222 |
| 5,185,258 | 2/1993 | Caldwell et al. | 435/220 |

FOREIGN PATENT DOCUMENTS

| | | |
|---|---|---|
| 0130756 | 1/1985 | European Pat. Off. . |
| 0328229 | 8/1989 | European Pat. Off. . |
| 0398539 | 11/1990 | European Pat. Off. . |
| 0405901 | 1/1991 | European Pat. Off. . |
| 0416967 | 3/1991 | European Pat. Off. . |
| 0516200 | 12/1992 | European Pat. Off. . |
| WO89/06279 | 7/1989 | WIPO . |
| 8906279 | 7/1989 | WIPO . |
| WO91/00345 | 1/1991 | WIPO . |
| 9219729 | 11/1992 | WIPO . |

*Primary Examiner*—Christine Skane
*Assistant Examiner*—Kery Fries
*Attorney, Agent, or Firm*—Steve T. Zelson; Elias J. Lambiris

[57] ABSTRACT

This invention relates to a detergent composition comprising an alkyl sulphate and one or more subtilisins and/or subtilisin variants, wherein said subtilisins and subtilisin variants have a glutamic acid residue in position 195 and/or an alanine residue in position 222.

14 Claims, 3 Drawing Sheets

DETERGENT COMPOSITION COMPRISING AN ALKYL SULFATE AND A SUBSTILISIN VARIANT

TECHNICAL FIELD

This invention relates to detergent compositions. More specifically, the invention relates to detergent compositions containing alkyl sulphate and one or more subtilisins or subtilisin variants, which subtilisins or subtilisin variants either in position 195 hold a glutamic acid residue, or in position 222 hold an alanine residue, or both.

BACKGROUND ART

Alkyl sulphate (AS) is an anionic surfactant used in various detergent compositions, often in mixtures with other anionic surfactants, especially linear alkylbenzene sulfonates (LAS). Anionic surfactants are known to provide excellent cleaning performance, and in numerous patent publications the use of AS as detergent ingredient is described, vide e.g. EP 219,314; EP 220,024; and EP 328,184.

In detergent compositions the use of AS is solely due to its superior detergency performance. It was certainly not to be anticipated that AS should have any positive influence on some detergent enzymes, while not on others. However, it has now surprisingly been found that AS exerts a positive influence on the performance of a specific group of detergent enzymes.

SUMMARY OF THE INVENTION

It has now been found that AS, when present, is able to increase the washability of certain detergent enzymes. These detergent enzymes belong to a group of subtilisins holding a glutamic acid residue and/or an alanine residue at specific positions.

Accordingly, the present invention provides a detergent composition comprising alkyl sulphate and one or more subtilisins or subtilisin variants, which subtilisins or subtilisin variants in position 195 hold a glutamic acid residue, and/or in position 222 hold an alanine residue.

BRIEF DESCRIPTION OF DRAWINGS

The present invention is further illustrated by reference to the accompanying drawings, in which.

DETAILED DISCLOSURE OF THE INVENTION

Figure 1:
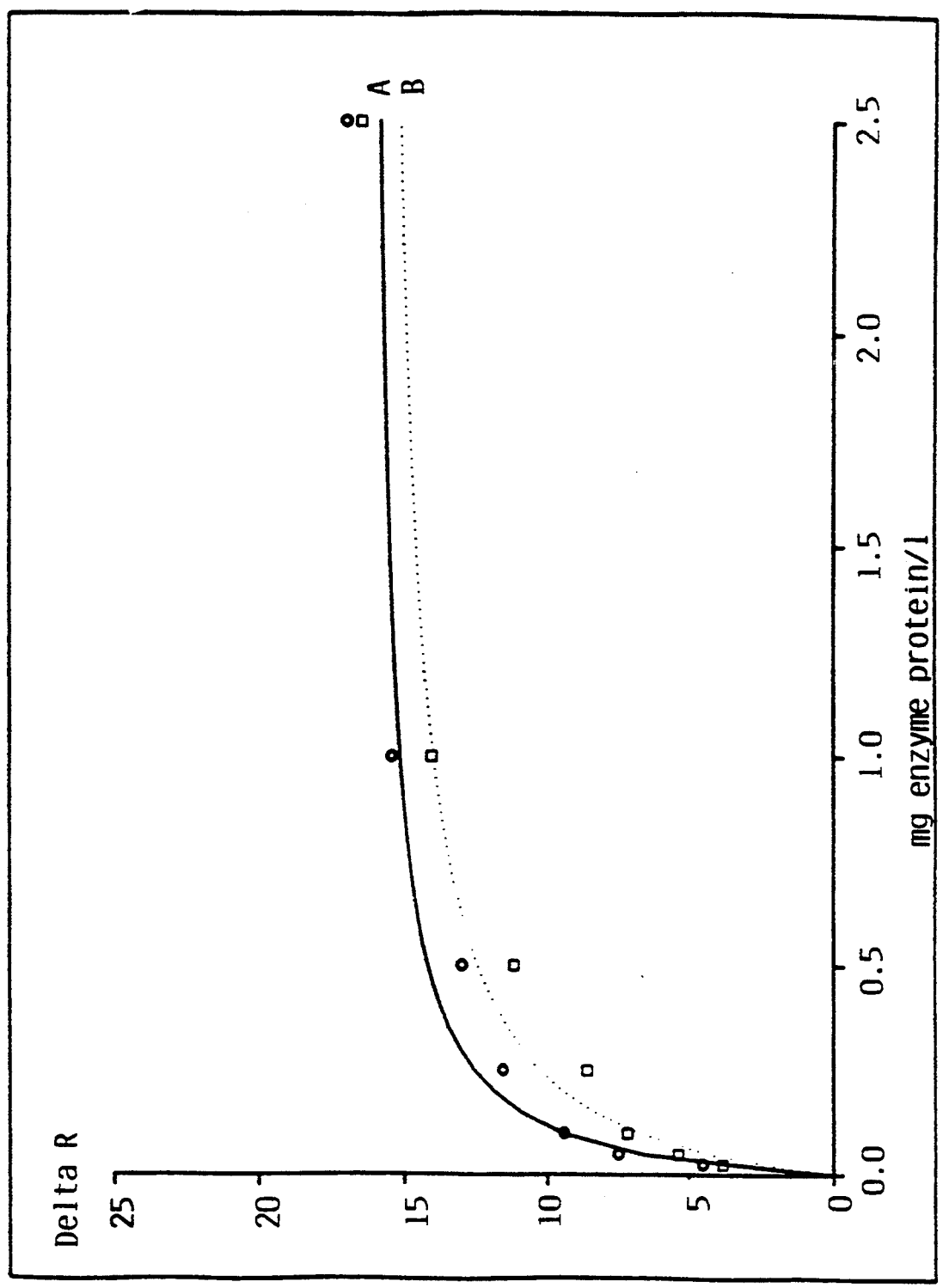
FIGS. 1–3 show a comparison of the wash performance of two detergent enzymes (A: Subtilisin 309/G 195E/M222A; and B: Subtilisin 309) in three different model detergents (Model I-III, respectively, cf. the Example; Grass juice soiled cotton, 10 min. at 20° C., 3°dH, and pH 10).

Experiments involving various detergent enzymes in various detergent compositions have now demonstrated that certain subtilisins show increased wash performance in the presence of alkyl sulphate. More investigations on this subject indicated that a glutamic acid residue and/or an alanine residue at certain specific positions are responsible for this effect.

In respect to definitions of subtilisins, reference is made to e.g. International Patent Publication Nos. WO 89/06279 and WO 91/00345. In these publications a survey of the amino acid sequence of various subtilisins is given. By alignment of the amino acid sequences of various subtilisins along with Subtilisin BPN' (Subtilisin NOVO) it is possible to allot a number to the amino acid residue position in any subtilisin, to the number of the analogous amino acid position in Subtilisin BPN', and hence to indicate the position of an amino acid residue in a subtilisin enzyme unambiguously.

Thus, referring to this numbering system, in the context of this invention referred to as "BPN' numbering", the above mentioned investigations indicate that a glutamic acid residue in position 195 and/or an alanine residue in position 222 (adjacent to the active serine at position 221 ) are responsible for the increased wash performance, when AS is present.

By a subtilisin variant, a mutated subtilisin, or a subtilisin derivative, is meant a subtilisin obtainable by alteration of a DNA nucleotide sequence of the parent gene or its derivatives. The subtilisin variant or mutated subtilisin may be expressed and produced when the DNA nucleotide sequence encoding the subtilisin is inserted into a suitable vector in a suitable host organism.

The subtilisin variant, mutated subtilisin or subtilisin derivative may also be a subtilisin that by way of e.g. protein engineering or by chemical or biological treatment is altered to produce a functionally equivalent derivative of said subtilisin, i.e. due to glycosylation or chemical stabilization.

In the context of this invention, when describing a mutation executed in a subtilisin, a specific nomenclature is adapted for ease of reference, the amino acid abbreviations being in accordance with the established one-letter code. According to this nomenclature, the substitution of e.g. glycine with glutamic acid in position 195 is designated as "Gly 195 Glu" or "G195E". If the substitution is made by mutation in e.g. Subtilisin 309, the product is designated "Subtilisin 309/G195E". A product involving two mutations can thus be designated "Subtilisin 309/G195E/-M222A".

A detergent composition of this invention comprises alkyl sulphate (AS) and one or more subtilisins or subtilisin variants in which the subtilisins or subtilisin variants hold a glutamic acid residue in position 195 and/or an alanine residue in position 222, and optionally the composition includes other detergent ingredients known in the art.

Within the scope of this invention are mutations or variants of the following subtilisins: Subtilisin BPN' (Wells et al. (1983); Proc. Natl. Acad. Sci. U.S.A. 84; 1219–1223; Wells et al. (1986); Phil. Trans. R. Soc. Lond. A. 317:415–423); Subtilisin Amylosachariticus (Kurihara et al. ( 1972); J. Biol. Chem. 247:5629–5631 ); Subtilisin 168 (Stahl and Ferrari ( 1984); J. Bacteriol. 159:811–819); Subtilisin Mesentericopeptidase (Svendsen et al. ( 1986); FEBS Lett 196:228–232); Subtilisin DY (Nedkov et al. ( 1985); Biol. Chem. Hoppe-Seyler 366:421–430); Subtilisin Carlsberg (Jacobs et al. ( 1985); Nucl. Acids Res. 13:8913–8926); Subtilisin 147 and Subtilisin 309 (International Patent Publication No. 89/06279); Subtilisin Thermitase from Thermoactinomyces vulgaris (Meloun et al. ( 1985); FEBS Lett. 1983:195–200); Proteinase K (Betzel et al. (1988); Eur. J. Biochem. 178:155ff; and Gunkel et al. (1989); Eur. J. Biochem. 179:185ff); Aqualysin (Kwon et al. (1988); Eur. J. Biochem. 173:491ff); Bacillus PB92 Protease (European Patent Publication No. 283,075); Protease TW3 and Protease TW7 (Tritirachium album) (International Patent Application No. PCT/US88/01040).

In respect to mutations and methods of producing mutations in the subtilisin gene, reference is made to e.g. International Patent Publication Nos. WO 89/06279 and WO 91/00345; European Patent Application Nos.

130,756, 251,446, 328,229, and 415,296; and U.S. Pat. No. 4,760,025.

Preferred subtilisins or subtilisin variants are mutations of Subtilisin BPN' (Subtilisin NOVO); Subtilisin Carlsberg; Subtilisin 309; or Subtilisin 147, and/or variants hereof, i.e. Subtilisin BPN'/M222A; Subtilisin Carlsberg/M222A; Subtilisin 147/M222A; Subtilisin 309/G 195E; Subtilisin 309/M222A; Subtilisin 309/G 195E/M222A; and/or variants hereof. Most preferred is Subtilisin 309/G195E/M222A, and/or variants hereof.

By the term AS is meant a non-ethoxylated alkyl sulphate, being linear or branched, and containing from 1 to 20 C-atoms, more preferably 10 to 20, most preferably 12 to 16 C-atoms.

In a detergent composition of the invention, the alkyl sulphate constitutes at least 5%, preferably at least 15%, more preferred at least 25%, yet more preferred at least 35%, most preferred at least 50%, of the total amount of anionic surfactant present.

Besides AS the detergent composition of the invention may comprise additional surfactant(s), which may be of an anionic, non-ionic, cationic, amphoteric or zwitter-ionic type, or a mixture of these. Typical examples of other anionic surfactants are linear alkyl benzene sulfonates (LAS); alpha olefin sulfonates (AOS); alcohol ethoxy sulfates (AES) and alkali metal salts of natural fatty acids. Examples of non-ionic surfactants are alkyl polyethylene glycol ethers; nonylphenol polyethylene glycol ethers; fatty acids esters of sucrose and glucose; and esters of polyethoxylated alkyl glucoside. In a specific embodiment of the invention, detergent compositions without any content of linear alkylbenzene sulfonates (LAS) are provided.

Other detergent ingredients known in the art include builders, bleaching agents, bleach activators, anti-corrosion agents, sequestering agents, anti soil-redeposition agents, perfumes, stabilizers for the enzymes and bleaching agents, formulations aids, optical brighteners, foam boosters, chelating agents, fillers, fabric softeners, etc. The detergent composition of the invention may be formulated substantially as described in J. Falbe [Falbe, J.; Surfactants in Consumer Products. Theory, Technology and Application; Springer Verlag 1987, Vide in particular the section entitled "Frame formulations for liquid/powder heavy-duty detergents"].

The detergent compositions of the invention can be formulated in any convenient form, such as powders, liquids, etc.

The detergent composition of the invention may advantageously include one or more other enzymes, e.g. lipases; amylases; cellulases; and/or peroxidases, conventionally included in detergent compositions.

The invention is further illustrated in the following example, which is not intended to be in any way limiting to the scope of the invention as claimed.

EXAMPLE

This example relates to a comparison of the influence of AS on the wash performance of two detergent enzymes: Subtilisin 309 and Subtilisin 309/G195E/M222A.

The wash performance tests were accomplished on grass juice soiled cotton in a model test, isothermically for 10 minutes at 20° C.

As detergents the following standard powder detergent compositions were used:

| (mg) | Model I (mg) | Model II | Model III (mg) |
|---|---|---|---|
| AS($C_{12-16}$) | 1230 | 615 | — |
| LAS (NANSA 80 S) | — | 615 | 1230 |
| AES | 107 | 107 | 107 |
| Alfa-olefin-suffonat | 67.8 | 67.8 | 67.8 |
| Soap | 108.3 | 108.3 | 108.3 |
| AE | 64.3 | 64.3 | 64.3 |
| Zeolit A | 930.5 | 930.5 | 930.5 |
| Sodium silicate | 160.7 | 160.7 | 160.7 |
| $Na_2SO_4$ | 128.6 | 128.6 | 128.6 |
| PEG 6000 | 64.3 | 64.3 | 64.3 |
| $Na_2CO_3$ | 546.4 | 546.4 | 546.4 |
|  | 3407 mg | 3407 mg | 3407 mg |

The detergent was dissolved in 4.5 liters of water of 3°dH (German Hardness), and the pH was measured to 10. The following enzyme dosages were used: 0.025; 0.05; 0.1; 0.25; 0.5; 1.0; and 2.5 mg protein/I.

The textile wash liquor ratio was approx. 6 g of textile per liter of wash liquor.

Subsequent to washing, the cloths were rinsed in running tap-water and air-dried. The remission (%R) was determined at 460 nm.

As a measure of the wash performance differential remission, A R was used being equal to the remission after wash with enzyme added, minus the remission after wash with no enzyme added.

Figure 2:
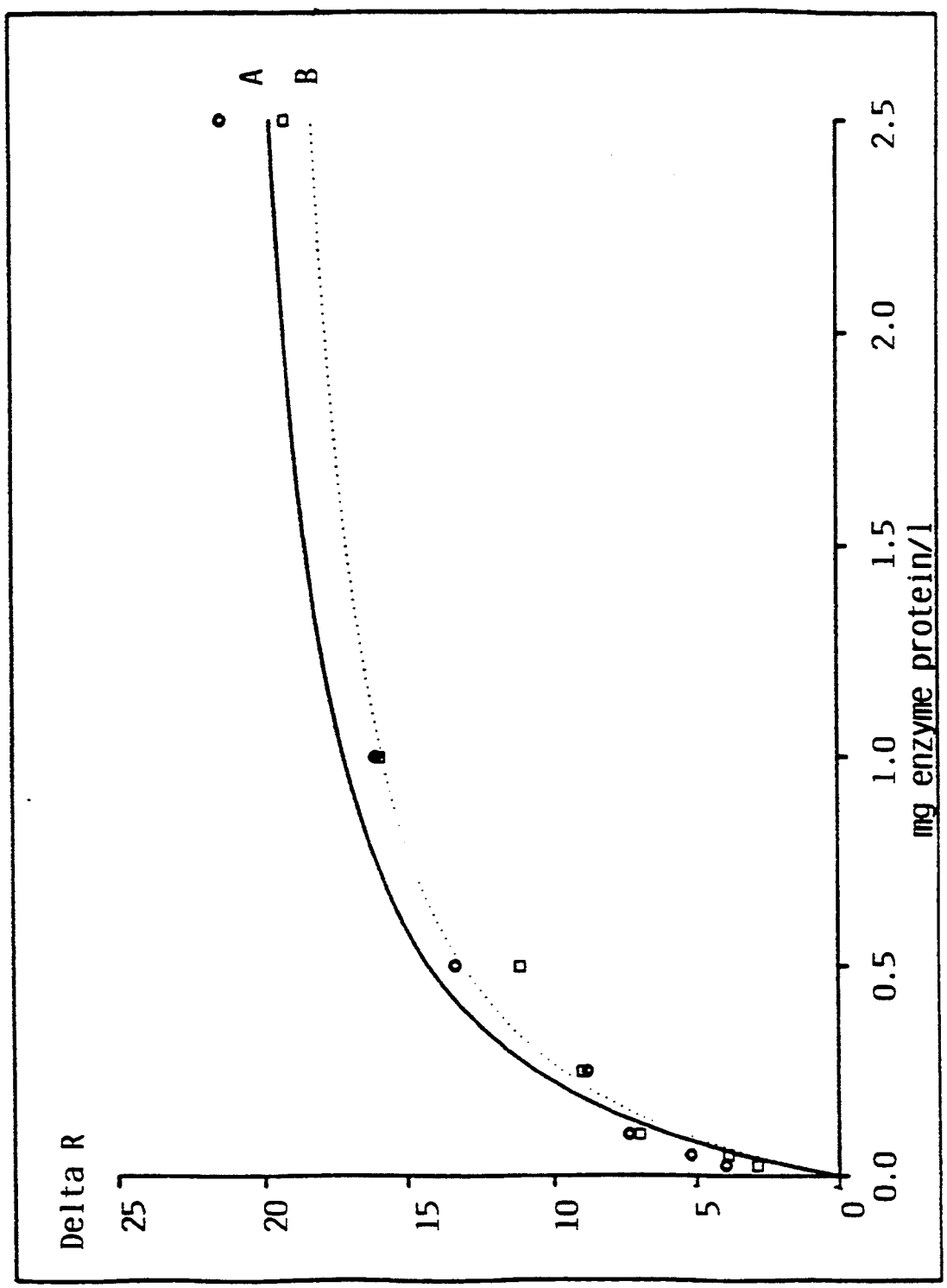
Figure 3:
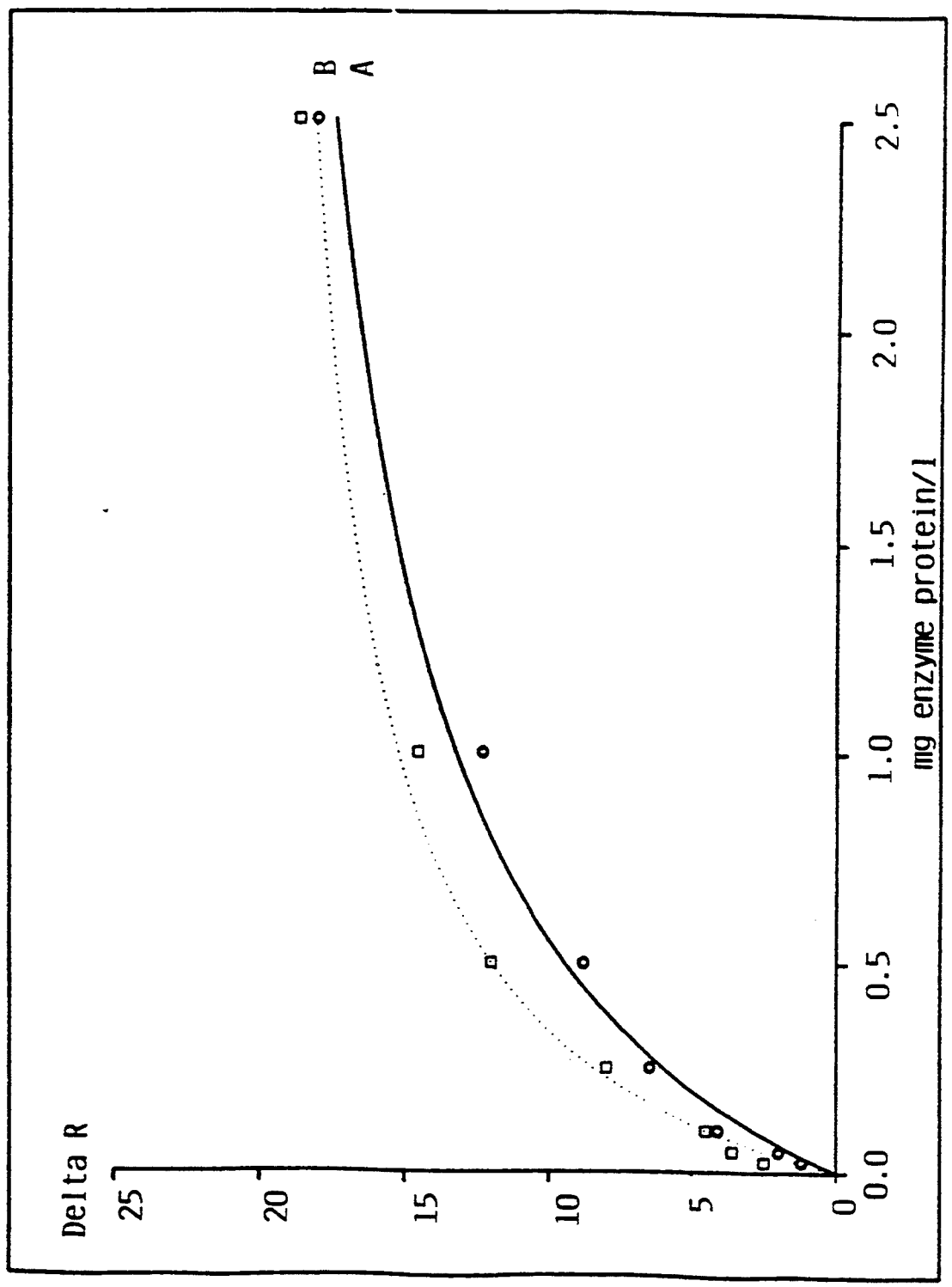

The results of this comparative test are shown in FIGS. 1-3 and in Table 1. In Table 1 the initial slope and the improvement factor (NB) with respect to the initial slope are calculated.

TABLE 1

| Detergent | AS/LAS-ratio | Initial slope A | B | $IF_a$ A/B |
|---|---|---|---|---|
| Model I | 36% AS/—LAS | 226.8 | 117.0 | 1.9 |
| Model II | 18% AS/18% LAS | 82.7 | 74.3 | 1.1 |
| Model III | —AS/36% LAS | 33.3 | 57.5 | 0.6 |

A: Subtilisin 309/G195E/M222A
B: Subtilisin 309
$IF_a$: Improvement factor (in respect to initial slope)

The figures and Table 1 clearly illustrate the washability boosting effect of a detergent composition of the invention.

We claim:

1. A detergent composition comprising an alkyl sulphate, one or more subtilisin variants selected from the group consisting of Subtilisin BPN'/M222A, Subtilisin Carlsberg/M222A, Subtilisin 147/M222A, Subtilisin 309/G195E, Subtilisin 309/M222A, and Subtilisin 309/G195E/M222A, and one or more other enzymes selected from the group consisting of amylases, lipases, cellulases and peroxidases.

2. The detergent composition according to claim 1, wherein the subtilisin variant is Subtilisin BPN'/M222A.

3. The detergent composition according to claim 1, wherein the subtilisin variant is Subtilisin Carlsberg/M222A.

4. The detergent composition according to claim 1, wherein the subtilisin variant is Subtilisin 147/M222A.

5. The detergent composition according to claim 1, wherein the subtilisin variant is Subtilisin 309/G195E.

6. The detergent composition according to claim 1, wherein the subtilisin variant is Subtilisin 309/.M222A.

7. The detergent composition according to claim 1, wherein the subtilisin variant is Subtilisin 309/G195E/M222A.

8. The detergent composition according to claim 1, wherein the alkyl sulphate constitutes at least 5 % (w/w) of the total amount of anionic surfactant present.

9. The detergent composition according to claim 1, wherein the alkyl sulphate constitutes at least 15 % (w/w) of the total amount of anionic surfactant present.

10. The detergent composition according to claim 1, wherein the alkyl sulphate constitutes at least 25 % (w/w) of the total amount of anionic surfactant present.

11. The detergent composition according to claim 1, wherein the alkyl sulphate is a $C_{1-20}$-alkyl sulphate.

12. The detergent composition according to claim 1, wherein the alkyl sulphate is a $C_{10-20}$-alkyl sulphate.

13. The detergent composition according to claim 1, wherein the alkyl sulphate is a $C_{12-16}$-alkyl sulphate.

14. The detergent composition according to claim 1, wherein no linear alkylbenzene sulfonate is present.

* * * * *